(12) United States Patent
Foerster

(10) Patent No.: US 6,520,980 B1
(45) Date of Patent: Feb. 18, 2003

(54) METHOD AND APPARATUS FOR ATTACHING CONNECTIVE TISSUES TO BONE USING A SELF-LOCKING KNOTLESS SUTURE ANCHORING DEVICE

(75) Inventor: Seth A. Foerster, San Clemente, CA (US)

(73) Assignee: Opus Medical, Inc., San Juan Capistrano, CA (US)

( * ) Notice: Subject to any disclaimer, the term of this patent is extended or adjusted under 35 U.S.C. 154(b) by 216 days.

(21) Appl. No.: 09/706,185

(22) Filed: Nov. 2, 2000

(51) Int. Cl.[7] .............................................. A61B 17/04
(52) U.S. Cl. ...................................................... 606/232
(58) Field of Search ........................... 606/232, 72, 77, 606/74, 75, 86, 220, 73, 228; 411/456, 508, 509, 913

(56) References Cited

U.S. PATENT DOCUMENTS

| | | |
|---|---|---|
| 3,143,916 A | 8/1964 | Rice |
| 4,301,551 A | 11/1981 | Dore et al. |
| 4,467,478 A | 8/1984 | Jurgutis |
| 4,483,023 A | 11/1984 | Hoffman, Jr. et al. |
| 4,590,928 A | 5/1986 | Hunt et al. |
| 4,597,776 A | 7/1986 | Ullman et al. |
| 4,605,414 A | 8/1986 | Czajka |
| 4,672,957 A | 6/1987 | Hourahane |
| 4,712,542 A | 12/1987 | Daniel et al. |
| 4,772,286 A | 9/1988 | Goble et al. |
| 4,823,780 A | 4/1989 | Odensten et al. |
| 5,195,542 A | 3/1993 | Gazielly et al. |
| RE34,293 E | 6/1993 | Goble et al. |
| 5,275,176 A | 1/1994 | Chandler |
| 5,324,308 A | 6/1994 | Pierce |
| 5,330,468 A | 7/1994 | Burkhart |
| 5,383,905 A | 1/1995 | Golds et al. |
| 5,441,508 A | 8/1995 | Gazielly et al. |
| 5,486,197 A | 1/1996 | Le et al. .................... 606/232 |
| 5,501,695 A | 3/1996 | Anspach, Jr. et al. |
| 5,545,180 A | 8/1996 | Le et al. .................... 606/232 |
| 5,573,548 A | 11/1996 | Nazre et al. |
| 5,575,801 A | 11/1996 | Habermeyer et al. |
| 5,584,835 A | 12/1996 | Greenfield |
| 5,584,839 A | 12/1996 | Gieringer |
| 5,591,207 A | 1/1997 | Coleman |
| 5,632,748 A | 5/1997 | Beck, Jr. et al. .......... 606/72 X |
| D385,352 S | 10/1997 | Bales et al. |
| 5,681,333 A | 10/1997 | Burkhart et al. |
| 5,690,649 A | 11/1997 | Li |
| 5,697,950 A | 12/1997 | Fucci et al. |
| 5,702,397 A | 12/1997 | Goble et al. |
| 5,707,394 A | 1/1998 | Miller et al. |
| 5,782,865 A | 7/1998 | Grotz |
| 5,797,963 A | 8/1998 | McDevitt |
| 5,810,854 A | 9/1998 | Beach |
| 5,860,978 A | 1/1999 | McDevitt |
| 5,868,789 A | 2/1999 | Huebner |
| 5,879,372 A | 3/1999 | Bartlett |

(List continued on next page.)

Primary Examiner—John J. Calvert
Assistant Examiner—Alissa L Hoey
(74) Attorney, Agent, or Firm—Stout, Uxa, Buyan & Mullins, LLP; Donald E. Stout

(57) ABSTRACT

An innovative bone anchor and methods for securing connective tissue, such as tendons, to bone, which permit a suture attachment that lies entirely beneath the cortical bone surface. Advantageously, the suturing material between the connective tissue and the bone anchor is secured without the need for tying a knot. The suture attachment to the bone anchor involves the looping of a length of suturing material around a self-locking wedge body in the anchor, thereby avoiding an eyelet connection which requires a knot and which concentrates stress on a very small portion of the suturing material. Thus, failure rates are greatly decreased over conventional techniques, and the innovative procedures are significantly easier to perform than conventional techniques.

14 Claims, 7 Drawing Sheets

U.S. PATENT DOCUMENTS

| | | |
|---|---|---|
| 5,893,850 A | 4/1999 | Cachia |
| 6,007,567 A | 12/1999 | Bonutti |
| 6,013,083 A | 1/2000 | Bennett |
| 6,022,373 A | 2/2000 | Li |
| 6,102,934 A * | 8/2000 | Li ............................... 606/232 |
| 6,146,406 A * | 11/2000 | Shluzas et al. .............. 606/232 |
| 6,328,758 B1 * | 12/2001 | Tornier et al. .............. 606/232 |
| 6,355,053 B1 * | 3/2002 | Li ............................... 606/232 |

* cited by examiner

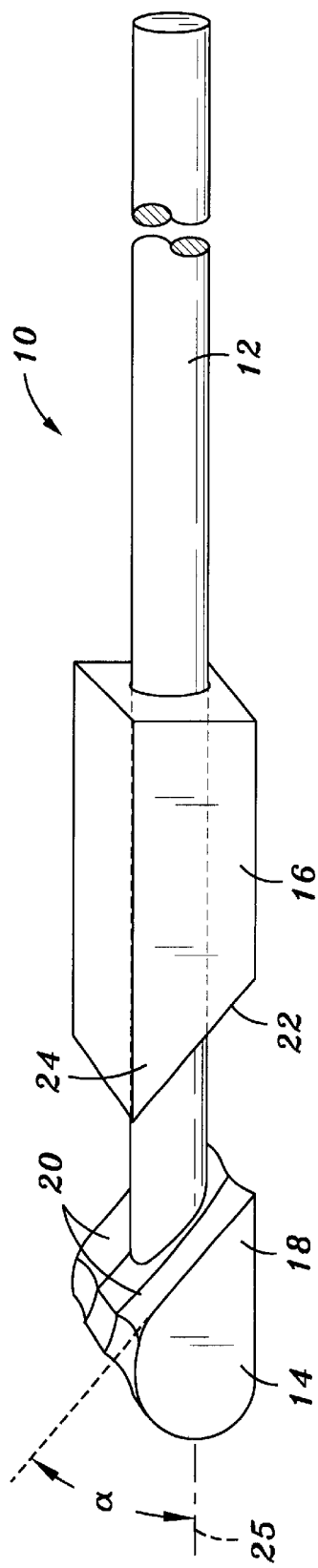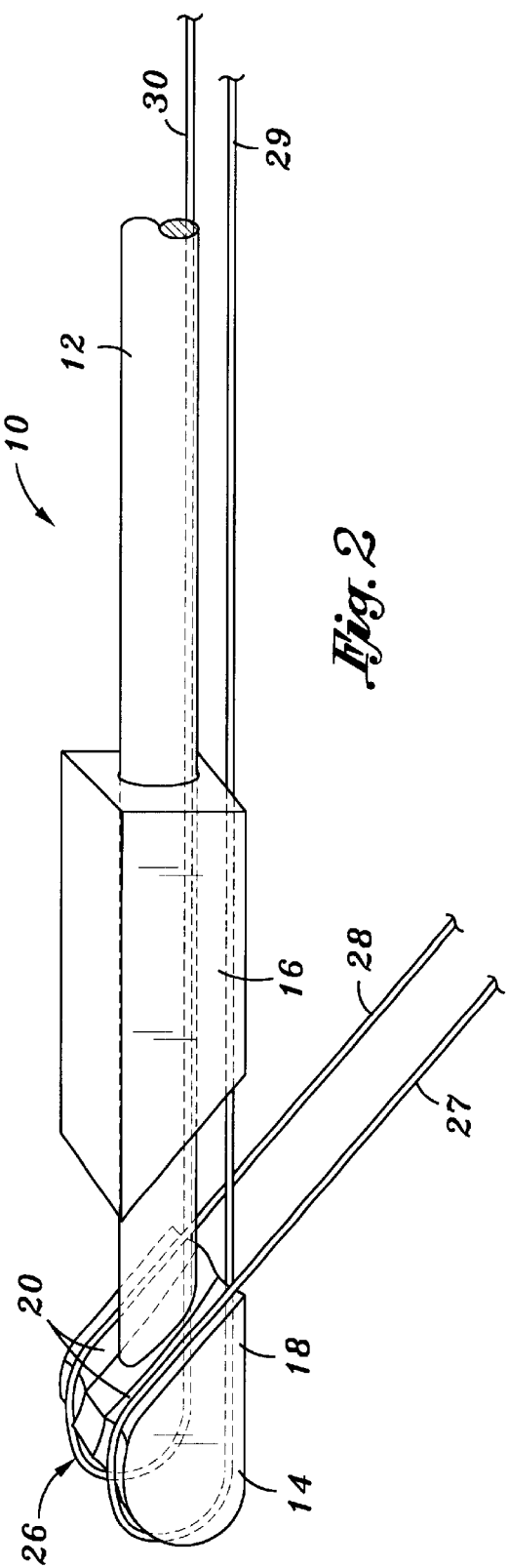

METHOD AND APPARATUS FOR ATTACHING CONNECTIVE TISSUES TO BONE USING A SELF-LOCKING KNOTLESS SUTURE ANCHORING DEVICE

The application is related to application Ser. No. 09/651,253, entitled Method & Apparatus for Attaching Connective Tissues to Bone Using a Knotless Suture Anchoring Device, filed on Aug. 30, 2000, which is commonly assigned and herein expressly incorporated by reference.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it is able to be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures are of the arthroscopic type, and are considered investigational in nature.

Another significant difficulty with current arthroscopic rotator cuff repair techniques are shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the. hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, breaking the sutures.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

What is needed, therefore, is a new approach for repairing the rotator cuff or fixing other soft tissues to bone, wherein suture tension can be adjusted and possibly measured, the suture: resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention solves the problems outlined above by providing innovative bone anchor and connective techniques which permit a suture attachment which lies entirely beneath the cortical bone surface. In the present state of the art, the sutures which are passed through the tissues to be attached to bone typically are threaded through a small eyelet incorporated into the head of the anchor and then secured by tying knots in the sutures. Endoscopic knot tying is an arduous and technically demanding task. Therefore, the present invention discloses devices and methods for securing sutures to a bone anchor without the requirement of knot tying.

More particularly, there is provided a bone anchor device for attaching connective tissue to bone. This device comprises a first member having a proximal suture receiving surface, and a second member having a distal suture receiving surface which is adapted for engaging contact with the proximal suture receiving surface. An axis extends through both of the first and second members. Advantageously, one of the first and second members is axially movable relative to the other of the first and second members to clamp suturing material disposed between the proximal and distal suture receiving surfaces. The inventive anchoring device further comprises a shaft, with the first member being fixed to a distal end of the shaft and the second member being disposed on the shaft, proximally of the first member. The second member is preferably movable along the shaft, relative to the first member. In one embodiment, the proximal suture receiving surface comprises a concave curved surface, and the distal suture receiving surface comprises a curved convex surface which is complementary to the distal suture receiving surface. In a presently preferred embodiment, however, the proximal suture receiving surface is a sloping surface, as is the distal suture receiving surface. The slopes of each of the suture receiving surfaces are preferably complementary to one another, for close engaging contact to clamp suture therebetween. In preferred embodiments, each of the proximal and distal suture receiving surfaces has a slope of between zero and about twenty degrees from the axis, with twelve degrees being most preferred in the case of stainless steel embodiments.

In another aspect of the invention, there is disclosed a method for securing connective tissue to bone. This inventive method comprises a step of securing a first end of a length of suture to a portion of soft tissue to be attached to a portion of bone. A second end of the length of suture is threaded about a suture receiving wedge body which forms a part of an inventive suture anchoring device. The wedge body is then placed in a blind hole disposed in the portion of bone. The second end of the length of suture is pulled proximally, so that the suture travels about the suture receiving wedge body and draws the first end of the length of suture toward the bone anchor device, thereby securing the portion of soft tissue snugly to the portion of bone. Thus, as a result, when the tension on the first end of the length of suture increases, as the portion of soft tissue is bound to the portion of bone, the suture receiving wedge body and a proximally disposed wedge seat member are moved relative to one another to engage one another, to thereby clamp a portion of the length of suture between the suture receiving wedge body and the proximally disposed wedge seat member.

The invention, together with additional features and advantages thereof, may best be understood by reference to the following description taken in conjunction with the accompanying illustrative drawing.

BRIEF DESCRIPTION OF THE DRAWINGS

FIG. 1 is a perspective view of an embodiment of a portion of a bone anchor having a suture lock constructed in accordance with the principles of the present invention;

FIG. 2 is a perspective view of the embodiment of FIG. 1, illustrating the inventive bone anchoring device with suturing material threaded therethrough;

DESCRIPTION OF THE PREFERRED EMBODIMENT

Figure 3:
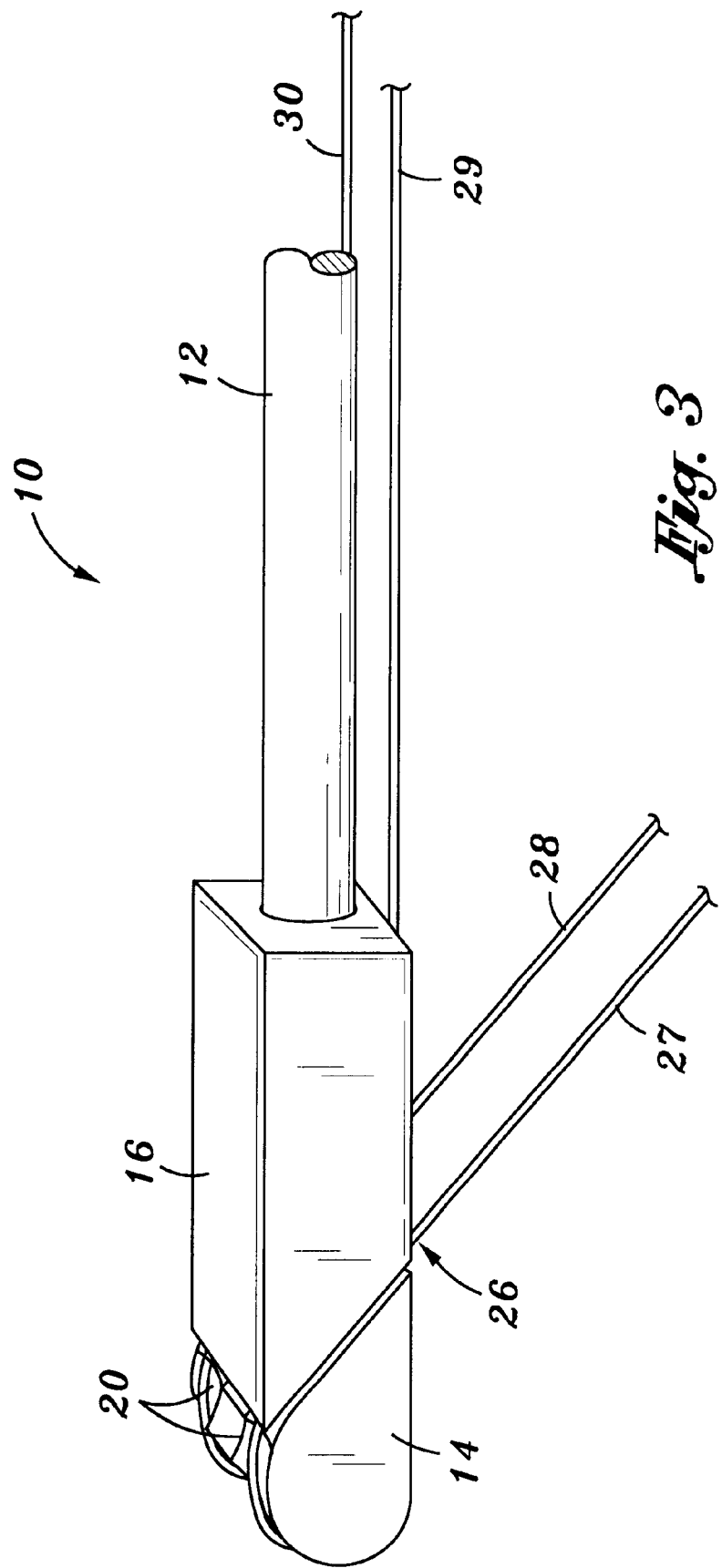
FIG. 3 is a perspective view showing the embodiment of FIG. 2 in its clamping orientation, wherein the suturing material is locked in place.

Referring now more particularly to the drawings, there is shown in FIG. 1 a bone anchor 10 constructed in accordance with a presently preferred embodiment of the invention, comprising a shaft 12 having a wedge body 14 disposed in a fixed position at its distal end. A wedge seat member 16 is disposed on the shaft 12 proximally of the wedge body 14. The wedge seat member 16 is disposed on the shaft 12 in such a manner that it may slide both in distal and proximal directions therealong as desired. It is noted that it is within the scope of the invention to make the wedge body 14 movable relative to the wedge seat member 16, making the member 16 the fixed element instead of the body 14, if desired. The wedge body 14 includes a tapered proximal end 18 and preferably has two suture receiving grooves or channels 20 disposed on its outer surface. The wedge seat member 16 also preferably comprises two suture receiving grooves or channels 22 (FIGS. 6A and 6B) which are adapted to correspond with the suture receiving grooves 20 when the wedge body 14 and wedge seat member 16 are in engaging contact with one another, as will be discussed in greater detail hereinbelow. The wedge seat member 16 includes a tapered distal end 24, which is tapered at an angle substantially corresponding to the taper angle of the tapered proximal end 18 of the wedge body 14. In preferred embodiments, the inventor has found that a taper angle a relative to a longitudinal axis 25 of the device 10, as shown in FIG. 1, should be between zero and approximately 20 0degrees for optimal performance. The optimal taper angle is directly related to coefficients of friction of the materials comprising the opposing engaging surfaces of the wedge body 14 and wedge seat member 16. In a case when both surfaces are comprised of stainless steel, the optimal taper angle a has been found to be about 12 degrees. For other materials, this optimal angle may vary, but there would be a definite fall-off in performance when the taper angle exceeds 20 degrees. The greater the angle a is above 20 degrees, the worse would be the resultant performance of the anchoring system.

Now with particular reference to FIG. 2, it may be seen how a length of suturing material 26 may be threaded through the bone anchor 10 prior to the insertion of the bone anchor 10 into desired bone structure. As shown, two free ends 27, 28 of the suture 26 have been threaded through the bone anchor, first passing along a bottom surface of the wedge seat member 16 and then along a bottom surface of the wedge body 14, in a proximal to distal direction. The free ends 27, 28 of the suture 26 are then wrapped about a distal end of the wedge body 14 along respective grooves 20, as shown. The suture ends 27, 28 are drawn downwardly between the wedge body 14 and the wedge seat member 16, as shown, and then proximally from a bottom edge of the anchor 10. The free ends 27, 28 may be grasped by the practitioner performing the procedure, and manipulated as desired.

The suturing material 26 also includes "bound" ends 29, 30, respectively, which, for purposes of this discussion, have already been stitched through a portion of soft tissue or tendon (not shown) using conventional suturing techniques already known in the art, or, alternatively, those techniques which are discussed in co-pending U.S. patent application Ser. No. 09/547,171, entitled Dual Function Suturing Apparatus & Method, filed on Apr. 11, 2000, or U.S. patent application Ser. No. 09/668,055, entitled Linear Suturing Apparatus & Method, filed on Sep. 21, 2000, both commonly assigned with the present application and expressly incorporated by reference herein. In presently preferred embodiments, the desired stitch is a so-called "mattress stitch", and it will be apparent to those skilled in the art that the bound suture ends 29, 30 are opposing ends of a portion of looped suture, comprising the stitch, which extends through the soft tissue portion. What is important to keep in mind at present is not the specific stitch employed, but rather that the suturing material is preferably stitched through the soft tissue before the above described threading process takes place, preferably outside of the patient's body.

FIG. 3 illustrates how the device 10 creates a self-locking mechanism. When it is desired to lock the suture 26 in place, the wedge seat member 16 may be pushed distally along the shaft 12, using a suitable tool (not shown), until it contacts the wedge body 14, thus pinching portions of the suture ends 27, 28 disposed in the grooves 20 between the wedge body 14 and the wedge seat member 16. As a result, the suture 26 is clamped firmly in place simply by continuing to exert a proximal force.

Figure 4:
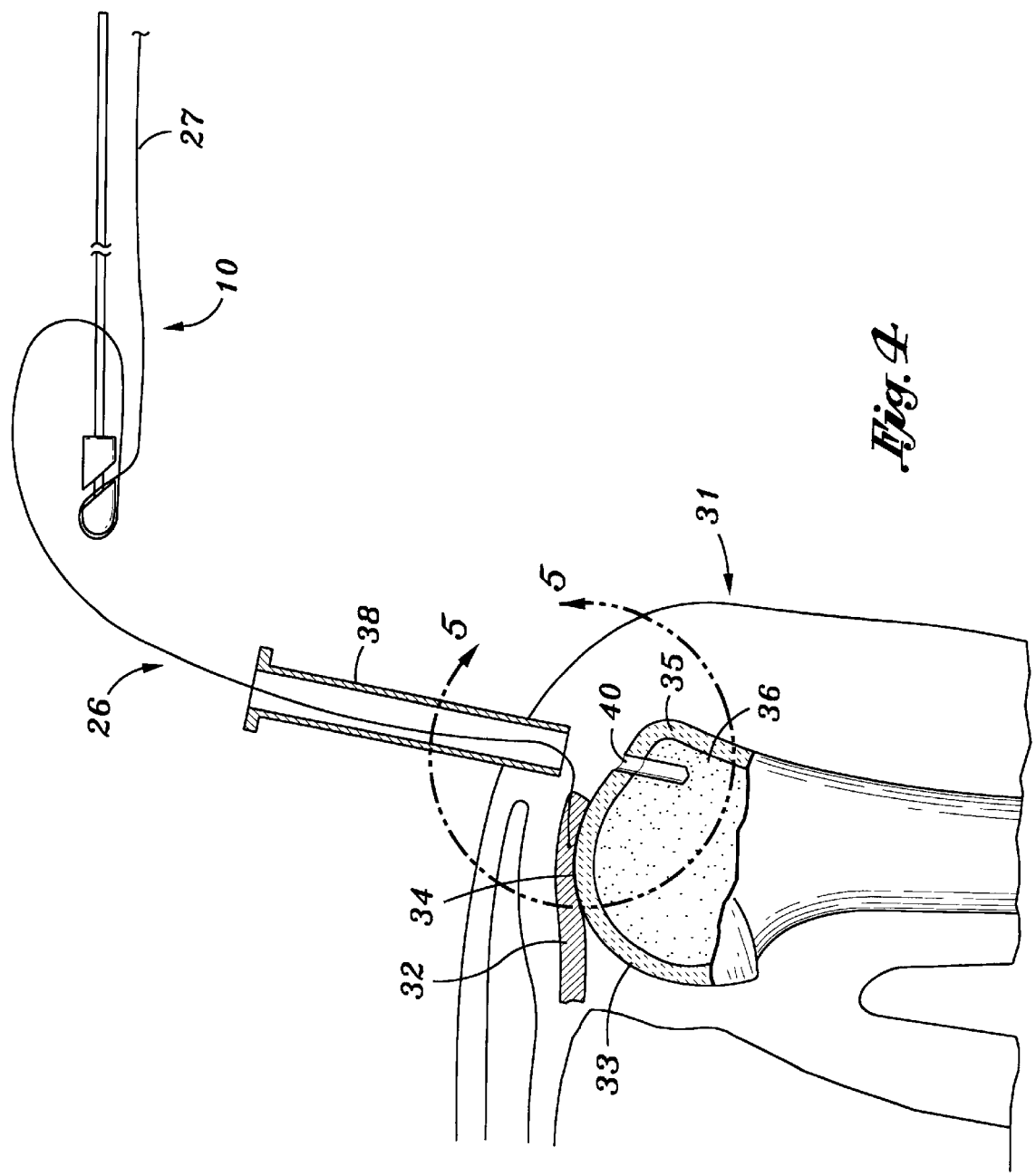
FIG. 4 is a schematic plan view, illustrating a first step in a preferred method for using the embodiment of FIGS. 1–3.

Referring now to FIGS. 4–7, a method for using the bone anchor device 10 to secure soft tissue to bone is shown and will be described hereinbelow. In FIG. 4, there is shown a schematic cross-sectional view of a human shoulder 31 on the left side of a patient's body as seen from the front, illustrating a rotator cuff tendon 32 which is disposed across a humeral head 33. It is to be understood that, due to injury or wear and tear on the joint, the rotator cuff tendon 32 has become detached from the humeral head 30 at the interface 34 between the two. The humeral head 33 is comprised of an outer surface of cortical bone 35 and inner cancellous bone 36. A trocar 38 has been inserted into the shoulder 31 in proximity to the area where the rotator cuff tendon 32 is to be reattached to the humeral head 33, in order to permit arthroscopic access to the procedural site. A blind hole 40 has been made, preferably by drilling or punching, in the desired location through the cortical bone 34 and into the cancellous bone 36. This illustration is intended only to provide a simple structural overview of the physiological elements involved in a typical situation where it is desired to reattach soft tissue such as rotator cuff tendon 32 to a humeral head 30. Although the preferred repair procedure discussed herein is an arthroscopic procedure, the inventive device may also be utilized in an open surgical procedure, if desired, wherein the sutures are manually placed.

Figure 5:
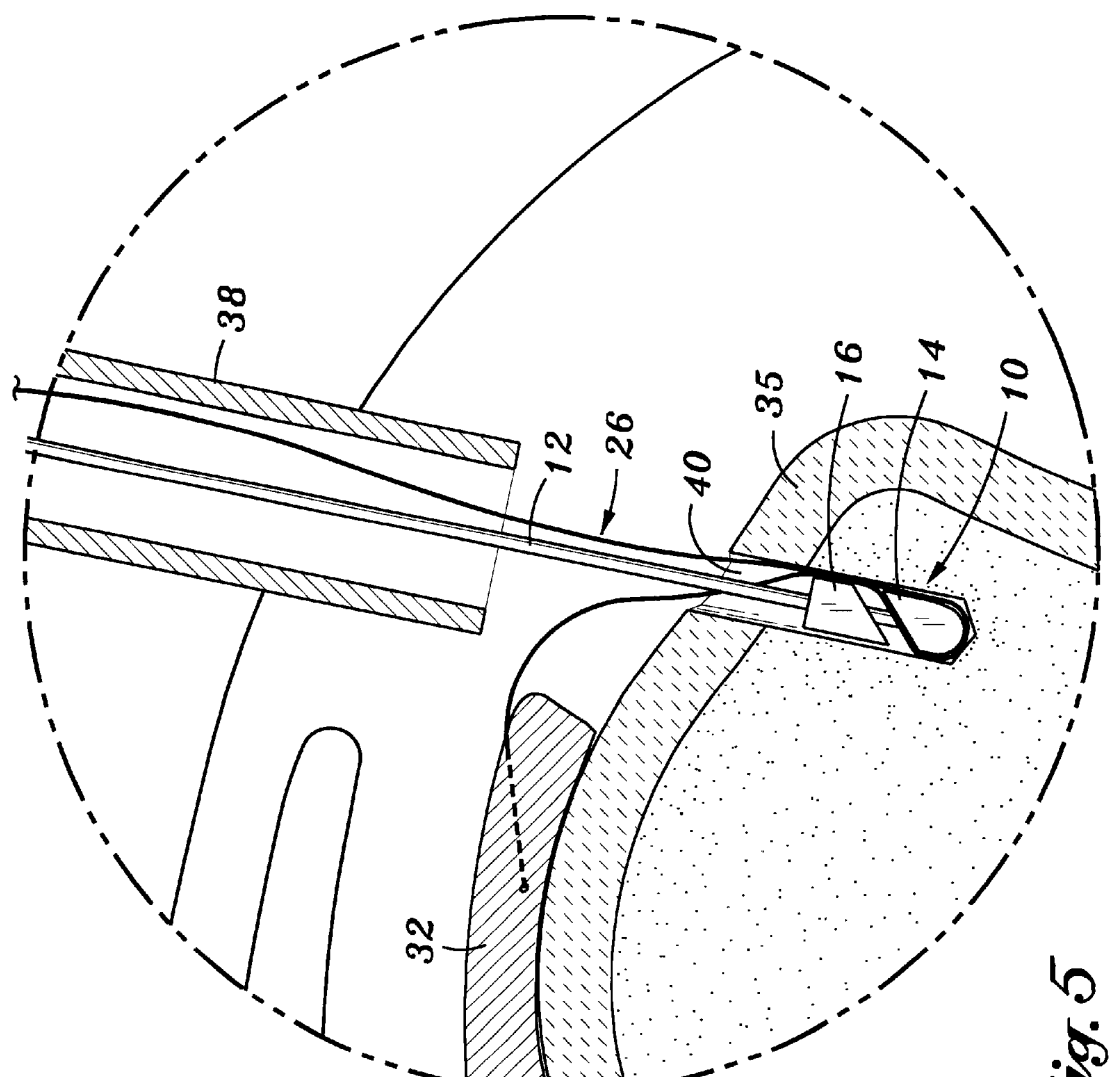
FIG. 5 is a detail view of the portion of FIG. 4 denoted by the region 5—5.

With reference still to FIGS. 4 and 5, it can be seen that the length of suture 26 has been stitched through the tendon 32, wherein the free ends 27, 28 of the suture pass through the trocar 38 and out of the shoulder, being threaded through the bone anchor 10 as previously described in connection with FIGS. 2 and 3 supra. The stitching process may be accomplished by any known means, as discussed supra, and any known suture stitch may be employed, the objective being to ensure a secure stitch so that the suture is not inadvertently separated from the tendon after completion of the repair procedure, necessitating re-entry to the surgical site. In preferred approaches, the suture is attached to the soft tissue using a "mattress stitch", which is well known in the art as being a particularly secure stitch which is unlikely to fail postoperatively.

FIG. 5 illustrates how the bone anchor 10 is inserted through the trocar 38 and into the hole 40 which has been made into the humeral head 33. It can be seen that the suture 26 has been drawn tightly against the bone anchor 10 by applying a continual proximal tension to the free ends 27, 28 of the suture 26 as the bone anchor is inserted. This proximally applied tensile force on the free ends of the suture 26 eliminates any slack at the fixation point of the suture 26 to the bone anchor 10 as well as creates tension from the distal or "bound" ends 29, 30 of the suture, which are secured to the tendon 32 by the aforementioned stitch. Once the bone anchor 10 has been inserted into the hole in the humeral head, the wedge seat member 16 is anchored securely to the bone structure, leaving only the shaft 12 and the wedge body 14 able to move freely in either a proximal or distal direction. Many different methods may be employed to anchor the wedge seat member 16 to the bone structure, which are well known to those of ordinary skill in the art. However, the specific means for anchoring the bone anchor 10 to the bone of the humeral head 33 is beyond the scope of this description.

Referring still to FIG. 5, the self-locking mechanis of the invention is further illustrated. With the wedge seat member 16 anchored securely to the bone, tension is applied to the suture 26 by pulling proximally on its free ends. As the tension is increased, selectively, by the practitioner, the proximal force on the wedge body 14 increases while the distal force on the wedge seat member increases. In turn, the pinching force on the suture disposed between the wedge body 14 and the wedge seat member 16 also increases, clamping the suture 26 between the wedge body 14 and the wedge seat member 16 and preventing the suture from moving in a distal direction. Importantly, the free ends 27, 28 of the suture may continue to be manipulated to adjust the size of the suture loop that is stitched through the tendon by pulling proximally on the free ends.

Figure 6B:
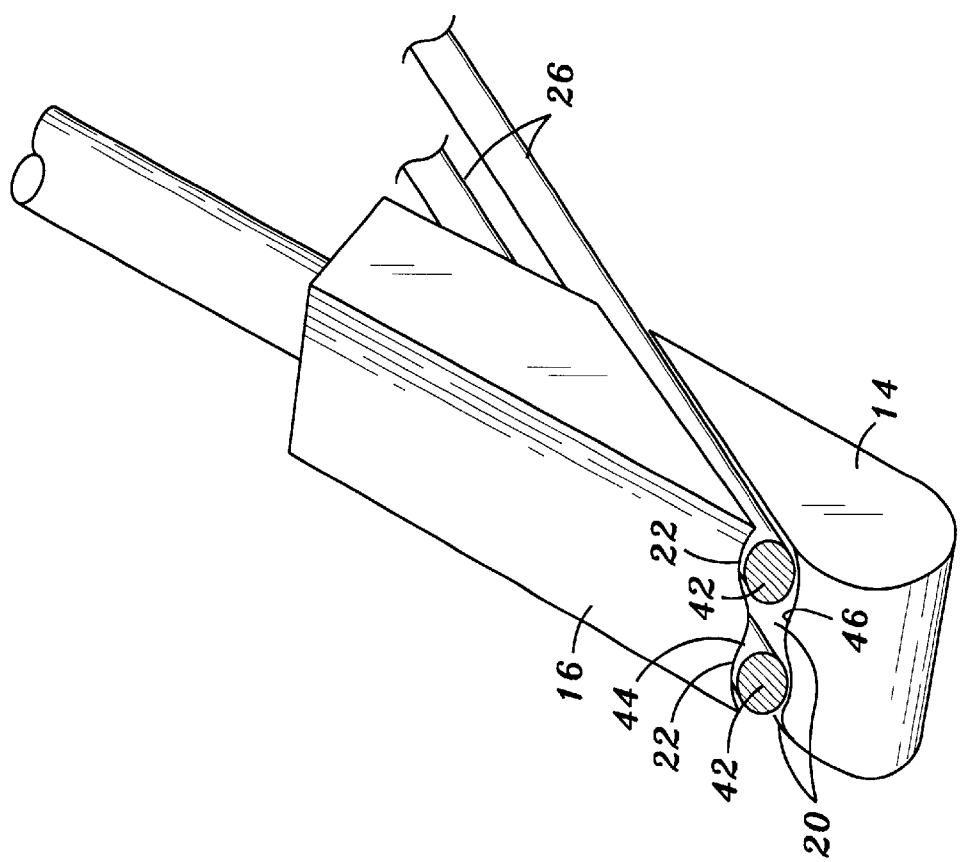
FIGS. 6A and 6B are perspective views of the distal end of the inventive anchoring device, illustrating the effect of the clamping force exerted by the device in its clamping orientation on the clamped portion of the suturing material threaded therethrough.
Figure 6A:
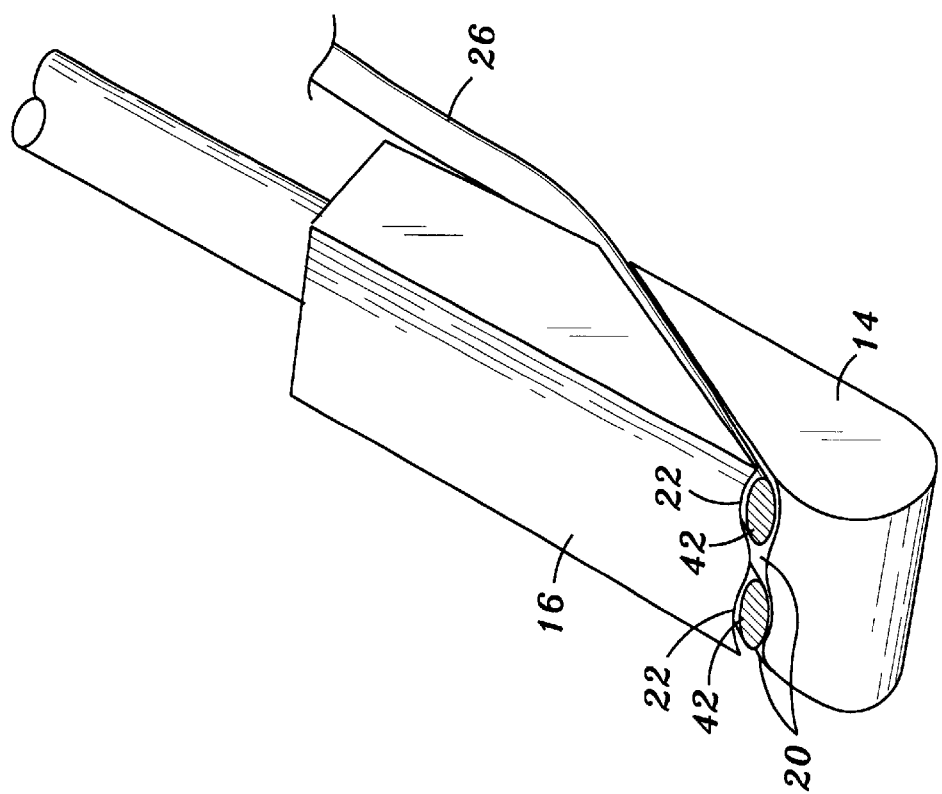

FIGS. 6A and 6B illustrate the effects of this clamping force on the length of the suture 26 in the case where a typical #2 suture material having a round configuration, with a cross-sectional width of approximately 0.023 inches, is utilized. As shown in FIG. 6A, the clamping force exerted by the wedge seat member 16 against the wedge body 14 causes the cross-sectional area of the suture 26 to compress to a more or less flattened configuration 42, having a cross-sectional width of approximately 0.011 inches. When a tensile force is then applied to the free ends 27, 28 of the suture 26, the suture tends to straighten out, which process causes it to push against the distal face of the wedge seat member 16 in a proximal direction, separating the wedge body 14 and the wedge seat member 16 a modest additional distance. Continued tension on the free ends of the suture 26 results in a return of the cross-sectional area of the clamped suture portion from the reduced flattened cross-sectional area shown in FIG. 6A to the original larger rounded cross-section 44 as shown in FIG. 6B. This rounding effect reduces the surface contact of the suture with the grooved faces of the wedge body 14 and the wedge seat member 16, thus reducing the frictional interface between the suture and the engaging groove faces and making it easier for the suture 26 to slide freely until a desired adjustment has been made. Once the tensile force is released, however, the suture will again be firmly clamped between the wedge body 14 and the wedge seat member 16 and is prevented from moving distally as explained supra.

Although any surface may be utilized for the grooves 20, 22 on the wedge body 14 and the wedge seat member 16, the preferred embodiment, as illustrated by FIGS. 6A and 6B, utilizes a profiled surface for such grooves, specifically a surface comprised of a combination of a concave area 44 and a convex area 46, for example. The use of this profiled surface reduces even further the surface contact of the suture 26 with the grooved faces of the wedge body 14 and the wedge seat member 16, as described above, thereby permitting the suture 26 to slide between them more easily than if a simple smooth surface were used.

Figure 7:
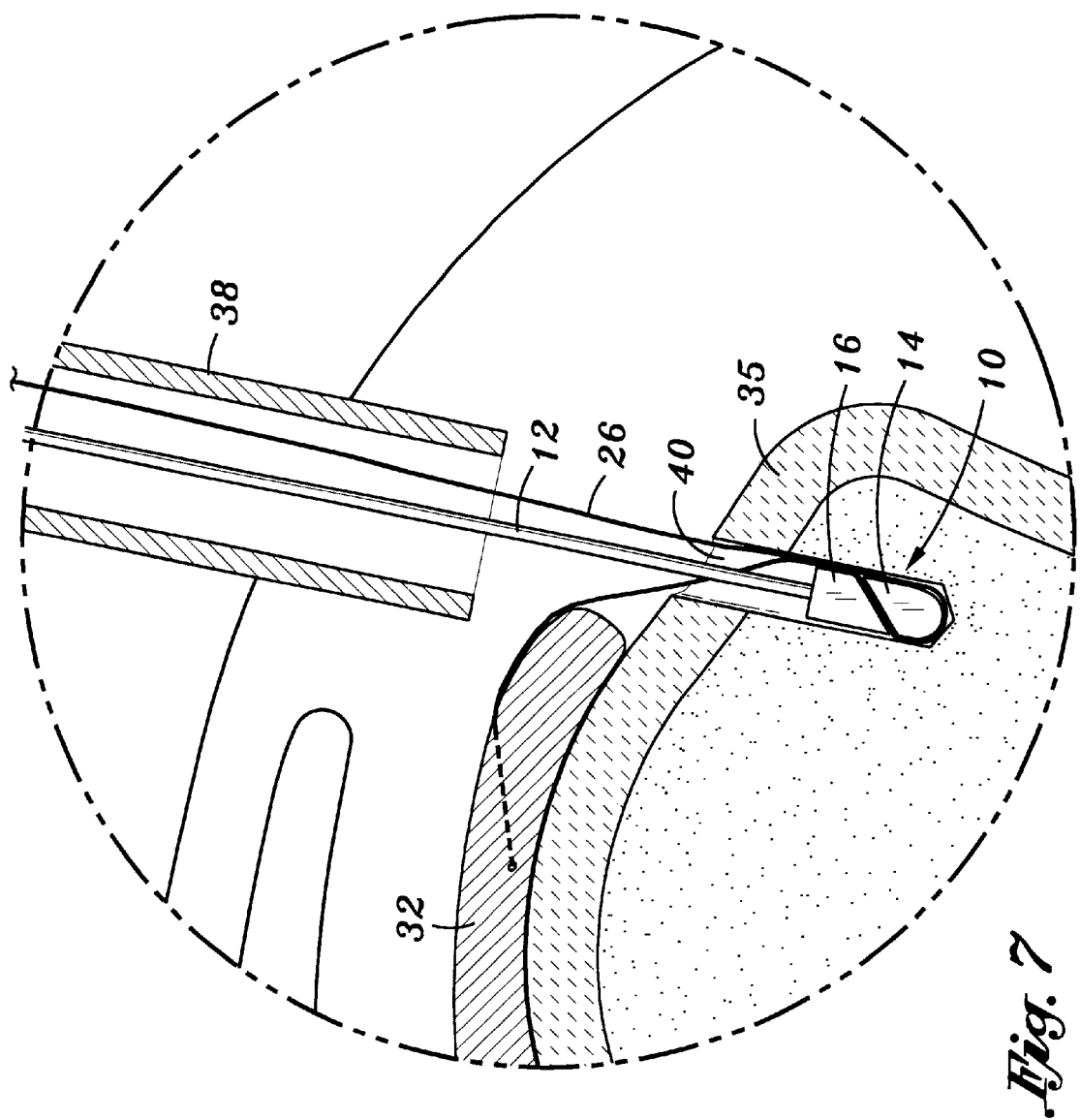
FIG. 7 is a detail view similar to FIG. 5, illustrating the anchoring device in its clamping orientation, after the suturing material has been locked in place.

FIG. 7 illustrates the manner in which the self-locking mechanism of the bone anchor 10 permits the practitioner to reattach soft tissue such as a rotator cuff tendon 32 to a bone such as the humeral head 33. Simply by applying a proximally directed tensile force to the free ends 27, 28 of the suture 26, the rotator cuff tendon 32 is pulled into a desired position in approximation with the humeral head 33. One of the significant advantages of this approach is its ability to permanently lock the bound ends 29, 30 of the suture 26 in place, but to also permit continued adjustability of the suture merely by applying a proximally directed tensile force to its free ends. This is important, because a practitioner will often find that, during the course of a procedure, after the tendon has been brought into what is believed to be a desired position relative to the bone to which it is being secured, and the suture has been locked into place to retain the tendon in that desired orientation, a further adjustment is necessary or desired to optimize the outcome. Using existing prior art solutions, though, wherein the suture is knotted into position and fixed at a particular length, it would be necessary to either forego the desired adjustment or, alternatively, to cut the suture:and re-suture the tendon.

With the present invention, after the free ends of the suture 26 have been pulled sufficiently that a tension is created in the bound end (due to approximation of the tendon to the bone), and the suture 26 has been clamped between the wedge body 14 and the wedge seat member 16, only the bound end of the suture is anchored in a fixed position. This ensures that the tendon 32 is not movable relative to the bone 33 after completion of the procedure, which of course is desirable. On the other hand, the free ends of the suture 26 continue to be movable, to thereby permit adjustment of the bound end, as desired. This permits adjustment or "fine tuning" of the position of the tendon 32 with respect to the bone 33.

Figure 8:
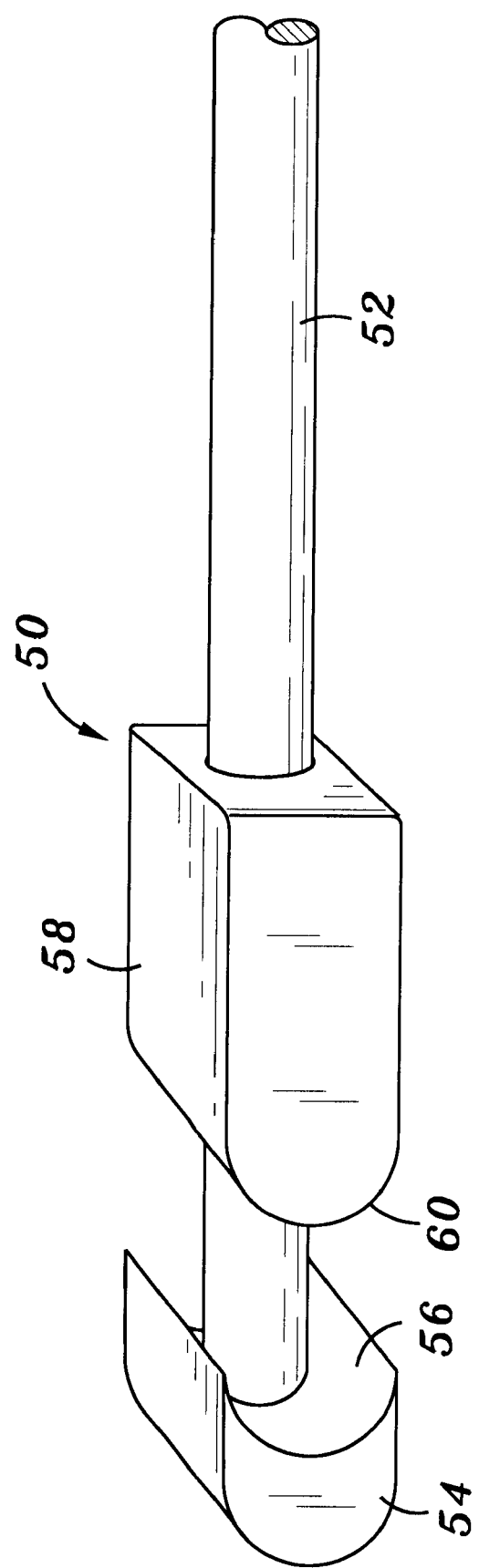
FIG. 8 is a perspective view of an alternative embodiment of the present invention.

In FIG. 8, there is illustrated an alternative embodiment of the present invention. A bone anchor 50, similar in shape and design to the embodiment illustrated in FIGS. 1–7, is shown, which comprises a shaft 52 with a fixed distal body 54 having a rounded body with a concave face 56, and a movable proximal body 58 having a convex distal face 60. This innovative design permits the threading of a suture therethrough, and for the suture to be locked into place once the device 50 has been inserted into a bone structure in substantially the same manner as in the embodiment of FIGS. 1–7. From this illustration, it can easily be seen that many different shapes or designs of the embodiment could be employed, any of which have, attached to a similar shaft, a fixed distal body which mates with a movable proximal body between which a suture may be threaded and locked into place.

It is to be understood that drawing figures and description above are illustrative in nature, and are not intended to perfectly reproduce the physiologic and anatomic nature of the human humeral head, nor to limit the application of the inventive embodiments to repair of the rotator cuff. The inventive apparatus ad methods are applicable to many different types of procedures involving, in particular, the attachment of connective or soft tissue to bone.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A bone anchor device for attaching connective tissue to bone, comprising:
   a first member having a proximal suture receiving surface;
   a second member having a distal suture receiving surface which is adapted for engaging contact with said proximal suture receiving surface;
   an axis extending through both of said first and second members; and
   a shaft, said first member being fixed to a distal end of said shaft and said second member being disposed on said shaft, proximally of said first member;
   wherein one of said first and second members is axially movable relative to the other of said first and second members to clamp suturing material disposed between said proximal and distal suture receiving surfaces.

2. The bone anchor device as recited in claim 1, wherein said second member is movable along said shaft, relative to said first member.

3. The bone anchor device as recited in claim 1, wherein said proximal suture receiving surface comprises a curved surface.

4. The bone anchor device as recited in claim 3, wherein said proximal suture receiving surface comprises a concave surface.

5. The bone anchor device as recited in claim 1, wherein said distal suture receiving surface comprises a curved surface.

6. The bone anchor device as recited in claim 5, wherein said proximal suture receiving surface comprises a convex surface which is complementary to said distal suture receiving surface.

7. The bone anchor device as recited in claim 1, wherein said proximal suture receiving surface is a sloping surface.

8. The bone anchor device as recited in claim 1, wherein said distal suture receiving surface is a sloping surface.

9. The bone anchor device as recited in claim 1, wherein said proximal and distal suture receiving surfaces are sloping surfaces, the slopes of each of said suture receiving surfaces being complementary to one another.

10. The bone anchor device as recited in claim 9, wherein each of said proximal and distal suture receiving surfaces has a slope of between zero and about twenty degrees from said axis.

11. The bone anchor device as recited in claim 9, wherein each of said proximal and distal suture receiving surfaces has a slope of about twelve degrees from said axis.

12. The bone anchor device as recited in claim 1, wherein each of said suture receiving surfaces includes a suture receiving groove.

13. The bone anchor device as recited in claim 12, wherein each of said suture receiving surfaces comprises a suture receiving groove having a concave portion and a convex portion.

14. A method for securing connective tissue to bone, comprising:

securing a first end of a length of suture to a portion of soft tissue to be attached to a portion of bone;

threading a second end of the length of suture about a suture receiving wedge body which forms a part of a suture anchoring device;

placing said wedge body in a blind hole disposed in said portion of bone; and pulling the second end of the length of suture proximally, so that the suture travels about the suture receiving wedge body and draws the first end of the length of suture toward the bone anchor device, thereby securing the portion of soft tissue snugly to the portion of bone;

wherein when the tension on the first end of the length of suture increases, as the portion of soft tissue is bound to the portion of bone, the suture receiving wedge body and a proximally disposed wedge seat member are moved relative to one another to engage one another, to thereby clamp a portion of the length of suture between the suture receiving wedge body and the proximally disposed wedge seat member.

\* \* \* \* \*